United States Patent
Frushour et al.

(10) Patent No.: US 11,065,062 B2
(45) Date of Patent: Jul. 20, 2021

(54) SYSTEMS AND METHODS OF TRACKING AND ANALYZING USE OF MEDICAL INSTRUMENTS

(71) Applicant: COVIDIEN LP, Mansfield, MA (US)

(72) Inventors: Scott E. M. Frushour, Boulder, CO (US); Ansel H. Dow, Eugene, OR (US)

(73) Assignee: COVIDIEN LP, Mansfield, MA (US)

( * ) Notice: Subject to any disclaimer, the term of this patent is extended or adjusted under 35 U.S.C. 154(b) by 368 days.

(21) Appl. No.: 15/597,708

(22) Filed: May 17, 2017

(65) Prior Publication Data
US 2018/0333209 A1    Nov. 22, 2018

(51) Int. Cl.
  *A61B 34/20*    (2016.01)
  *A61B 34/00*    (2016.01)
  (Continued)

(52) U.S. Cl.
  CPC ............. *A61B 34/20* (2016.02); *A61B 5/062* (2013.01); *A61B 18/1206* (2013.01);
  (Continued)

(58) Field of Classification Search
  CPC ..... A61B 34/20; A61B 5/062; A61B 18/1206; A61B 18/1445; A61B 34/25; A61B 2560/0266; A61B 2560/0462; A61B 2562/0271; A61B 2562/0223; A61B 2562/0219; A61B 2576/00; A61B 2034/2048; A61B 2562/0247; A61B 34/35; A61B 34/10; A61B 34/30; G16H 40/63
  See application file for complete search history.

(56) References Cited

U.S. PATENT DOCUMENTS

2004/0143261 A1*  7/2004  Hartley ............. A61B 18/1492
                                                   606/45
2007/0073136 A1*  3/2007  Metzger ............ A61B 17/1637
                                                   600/407
(Continued)

FOREIGN PATENT DOCUMENTS

CA      2957977 A1    4/2017
WO   2014063181 A1    5/2014
WO   2016029138 A1    2/2016

OTHER PUBLICATIONS

Harbison et al., An Automated Methodology for Assessing Anatomy-Specific Instrument Motion during Endoscopic Endonasal Skull Base Surgery, published online Dec. 20, 2016 (Year: 2016).*

(Continued)

*Primary Examiner* — Serkan Akar
*Assistant Examiner* — Aminah Asghar
(74) *Attorney, Agent, or Firm* — Carter, DeLuca & Farrell LLP

(57) ABSTRACT

A method for a medical procedure is provided and includes obtaining data from sensors disposed in a medical instrument. The sensors include at least one first sensor configured to measure acceleration, at least one second sensor configured to measure rotation, and at least one third sensor configured to measure direction of movement. The method further includes correlating the data from the sensors with time and storing the correlated data and time. A medical system, a method for imaging a medical procedure, and a method of processing sensor measurements are also disclosed.

20 Claims, 9 Drawing Sheets

(51) Int. Cl.
   *A61B 5/06* (2006.01)
   *A61B 17/00* (2006.01)
   *A61B 18/14* (2006.01)
   *A61B 18/12* (2006.01)
   *G16H 40/63* (2018.01)

(52) U.S. Cl.
   CPC .......... *A61B 18/1445* (2013.01); *A61B 34/25* (2016.02); *G16H 40/63* (2018.01); *A61B 2017/00084* (2013.01); *A61B 2017/00199* (2013.01); *A61B 2034/2048* (2016.02); *A61B 2034/256* (2016.02); *A61B 2560/0266* (2013.01); *A61B 2560/0462* (2013.01); *A61B 2562/0219* (2013.01); *A61B 2562/0223* (2013.01); *A61B 2562/0247* (2013.01); *A61B 2562/0271* (2013.01); *A61B 2576/00* (2013.01)

(56) References Cited

U.S. PATENT DOCUMENTS

| | | | |
|---|---|---|---|
| 2007/0103437 A1* | 5/2007 | Rosenberg | G09B 23/285 345/161 |
| 2008/0249467 A1* | 10/2008 | Burnett | A61B 17/3417 604/117 |
| 2011/0144640 A1* | 6/2011 | Heinrich | A61B 17/0469 606/41 |
| 2012/0083827 A1* | 4/2012 | Artale | A61B 17/285 606/207 |
| 2013/0064427 A1 | 3/2013 | Picard et al. | |
| 2014/0257274 A1 | 9/2014 | McCullough, Jr. et al. | |
| 2016/0038248 A1 | 2/2016 | Bharadwaj et al. | |
| 2016/0067007 A1* | 3/2016 | Piron | A61B 5/7246 705/3 |
| 2016/0249174 A1* | 8/2016 | Patel | A61B 5/01 |
| 2017/0079644 A1 | 3/2017 | Overmyer et al. | |
| 2017/0143440 A1* | 5/2017 | McGinley | A61B 90/06 |
| 2017/0245942 A1* | 8/2017 | Penenberg | A61B 6/463 |

OTHER PUBLICATIONS

European Office Action dated Oct. 18, 2018 issued in corresponding EP Appln. No. EP18172555.

* cited by examiner

SYSTEMS AND METHODS OF TRACKING AND ANALYZING USE OF MEDICAL INSTRUMENTS

BACKGROUND

Technical Field

The present disclosure relates to medical systems, and more particularly, to systems and methods for collecting, analyzing, and displaying data relating to the use of medical instruments.

Description of Related Art

As technology has advanced, medical instruments have also become more advanced. For example, surgeons have begun to replace classical open surgical techniques with minimally invasive techniques such as laparoscopic or thoracoscopic surgery in an effort to minimize trauma to surrounding tissue, reduce pain, reduce scarring, and reduce the length of time the patient is required to stay at the hospital. Minimally invasive surgery, such as the laparoscopic approach pioneered in the early $20^{th}$ century, involves the use of small incisions (from one to several), typically no larger than 5-10 mm. While performing these or similar procedures, the surgeon must be able to accurately determine the position of the surgical instrument relative to the tissue undergoing treatment. Typically, during an open procedure, the surgeon would have direct line of sight to the surgical instrument. However, with increasing reliance upon advanced medical procedures and instruments, such as minimally invasive techniques, it is often difficult or impossible for the surgeon to be able to identify the position of the surgical instrument within the patient.

To alleviate this issue, a distal portion of the laparoscopes utilized during laparoscopic surgery typically include a camera disposed thereon to enable the surgeon to visualize the surgical site. However, the narrow field of view provided by the camera necessarily focuses on only a small portion of the body cavity the surgeon is operating within. As such, the surgeon is often left to navigate the surgical tools within the body cavity using their knowledge of the patient's anatomy to conceptualize the operating space.

Concurrent with advances in surgical techniques, imaging modalities such as CT (including X-ray CT, computerized axial tomography (CAT) scan, positron emission tomography (PET), and single photon emission CT (SPECT)), Magnetic Resonance Imaging (MRI), Ultrasound, Flouroscopy, and others have been developed to enable a clinician to more accurately identify lesions or other medical conditions without the need for more invasive surgeries (such as an open approach).

Using the images obtained by one of the above noted imaging modalities, three-dimensional reconstructions of organs, anatomical structures, etc. can be developed and utilized by clinicians to segment various tissues from one another and assess an accurate location of the lesion within the thoracic or abdominal cavity. This segmentation further enables a clinician to determine the precise tissue segment with its affiliated organ and determine the ideal incision level for the minimally invasive procedure. Additionally, the three-dimensional model and precise identification of the lesion within the body cavity enables clinicians to identify an ideal location for port placement and develop a pathway through which the surgical instruments should be guided during the surgical procedure.

To aid the surgeon in navigating the surgical instrument within the body cavity and to further increase the surgeons ability to visualize the surgical space, a pathway through which the surgical instruments should be guided during the surgical procedure may be developed using the three-dimensional model and precise identification of the lesion within the body cavity, and further, to track the surgical instrument within the body cavity with respect to the three-dimensional model and generated pathway.

Although these technological advances have benefitted surgeons performing minimally invasive surgeries, only the position and orientation of the surgical instrument within the body cavity are typically indicated within the three-dimensional model. As can be appreciated, the precise position, heading, and orientation of the surgical instrument within the patient are of extreme importance to the surgeon, especially when navigating the surgical instrument relative to critical structures within the patient.

Notably, advances in medical technology pertaining to minimally invasive surgical techniques have mainly been directed towards improving surgeon's ability to perform the procedure, and not on how to educate surgeons on how to improve their techniques using existing medical instruments. Clinical education has mainly utilized textbook, visual, and hands on approaches to teaching surgeons how to perform minimally invasive surgeries. Due to the nature of minimally invasive surgical techniques, it is often difficult, if not impossible, to illustrate how the surgical technique is performed in real time. Specifically, the narrow field of view provided by the laparoscope inhibits surgeons from illustrating a more comprehensive view of the surgical landscape as the procedure is being performed. Notably, the orientation, heading, and direction the medical instrument is pointing within the body cavity of the patient are not easily visible. Therefore, it is difficult to educate clinicians using a visual approach and/or for surgeons to compare similar surgical procedures in an effort to further refine surgical techniques to increase efficiency, reduce the time to complete the procedure, reduce patient trauma, etc.

Accordingly, there is continued interest in improving medical instruments and medical technology to assist physicians and clinicians before, during, and after medical procedures.

SUMMARY

The present disclosure relates to collecting, analyzing, and displaying data relating to the use of medical instruments.

In certain aspects, the present disclosure is directed to a method for a medical procedure. The method includes obtaining data from one or more sensors disposed in a medical instrument. The sensors include at least one first sensor configured to measure acceleration, at least one second sensor configured to measure rotation, and at least one third sensor configured to measure direction of movement. The method further includes correlating the data from the sensors with time and storing the correlated data and time.

In aspects, the at least one first sensor may include an accelerometer. In some aspects, the at least one second sensor may include a gyroscope. In further aspects, the at least one third sensor may include a magnetometer. In certain aspects, the method may further include calibrating the magnetometer based on geographic location. In aspects, the one or more sensors may include at least one fourth sensor configured to measure pressure. The at least one fourth sensor may include a barometer. In other aspects, the method may further include calibrating the barometer based on at least one of elevation or local environmental conditions.

In some aspects, the method may further include determining that the medical instrument has entered the body cavity of a patient. In further aspects, determining that the medical instrument has entered the body cavity of a patient may include determining that measured pressure from the barometer exceeds a threshold. In other aspects, determining that the medical instrument has entered the body cavity of the patient may include determining that measured acceleration has decreased from above a first threshold to below a second threshold. In aspects, obtaining data from the sensors may include obtaining data from the sensors as the medical instrument is maneuvered within the body cavity of a patient.

In certain aspects, the method may further include storing data indicating a reference point, where the reference point is a point of entry into the body cavity of a patient. In some aspects, the method may further include displaying a representation of the reference point on a display screen, displaying a representation of a medical instrument, and animating movement of the representation of the medical instrument based on data from the sensors and the correlated time.

In further aspects, the method may further include associating the correlated sensor data with a particular patient, a particular clinician, and/or a particular medical procedure.

A further aspect of the present disclosure is directed to a medical system that includes at least one first sensor disposed in a medical instrument and configured to measure acceleration, at least one second sensor disposed in the medical instrument and configured to measure rotation, at least one third sensor disposed in the medical instrument and configured to measure direction of movement, a clock circuit configured to indicate time, a memory, and processing circuitry in communication with the at least one first sensor, the at least one second sensor, the at least one third sensor, and the clock circuit. The processing circuitry is configured to receive measured data of the at least one first sensor, the at least one second sensor, and the at least one third sensor, correlate the measured data with time indicated by the clock circuit, and store the correlated measured data and time in the memory.

In aspects, the at least one first sensor may be an accelerometer. In other aspects, the at least one second sensor may be a gyroscope. In certain aspects, the at least one third sensor is a magnetometer. In further aspects, the accelerometer may be configured to measure linear acceleration of the medical instrument, the gyroscope may be configured to measure at least rotation of the medical instrument about a longitudinal axis of the medical instrument, and the magnetometer may be configured to measure direction of the medical instrument based on a geomagnetic field. In some aspects, the at least one second sensor may be configured to measure at least one of yaw, pitch, or roll of the medical instrument.

In other aspects, the system may further include at least one fourth sensor disposed in the medical instrument that is configured to measure pressure. In aspects, the at least one fourth sensor may be a barometer. In certain aspects, the system may further include an integrated circuit disposed in the medical instrument that includes the at least one first sensor, the at least one second sensor, the at least one third sensor, and the at least one fourth sensor.

In further aspects, the memory may be configured to store a medical instrument identifier, a clinician identifier, and/or a medical procedure identifier. The stored identifier(s) may be associated with the measured sensor data.

In other aspects, the system may further include at least one fourth sensor disposed in the medical instrument that is configured to measure energy applied to a patient by the medical instrument.

In some aspects, the system may further include a trigger disposed on the medical instrument and in communication with the processing circuitry. The processing circuitry may be configured to determine an amount of time the trigger is actuated to determine an amount of energy applied to a patient by the medical instrument.

In aspects, the system may further include a trigger disposed on the medical instrument and in communication with the processing circuitry. The processing circuitry may be configured to register an actuation of the trigger and a release of the trigger to determine an amount of energy applied to a patient by the medical instrument.

In further aspects, the medical instrument may be an endoscopic electrosurgical instrument. In other aspects, the medical instrument may be a laparoscopic electrosurgical instrument.

In certain aspects, the processing circuitry may be configured to determine that a distal portion of the medical instrument has entered a body cavity of a patient based on measured pressure from the barometer exceeding a threshold. In some aspects, the system may further include a trigger disposed on the medical instrument and in communication with the processing circuitry. The processing circuitry may be configured to determine that a distal portion of the medical instrument has entered a body cavity of a patient when the trigger is actuated.

In aspects, the clock circuitry and the processing circuitry may be disposed in the medical instrument. In further aspects, the system may further include a computing device separate from the medical instrument where the clock circuitry and the processing circuitry are disposed in the computing device.

In other aspects, the system may further include a display screen and the processing circuitry may be further configured to display a representation of the medical instrument on the display screen and animate movement of the representation of the medical instrument based on the measured data and the correlated time.

Yet another aspect of the present disclosure is directed to a method for imaging a medical procedure including accessing an image of an anatomy of a patient, displaying the image on a display screen, accessing data from sensors disposed in a medical instrument, where the data includes measured acceleration, rotation, and direction of movement of the medical instrument, and the data is correlated with time. The method further includes translating data from the sensors to positional information of the medical instrument, displaying a representation of the medical instrument with the image of the patient anatomy on the display screen, and animating the representation of the medical instrument based on the data from the sensors and the correlated time. In aspects, the image of the patient anatomy may be a representation of the anatomy of the patient. In other aspects, the method may further include displaying a three-dimensional representation of the anatomy of the patient.

In certain aspects, displaying the representation of the medical instrument may include displaying a marker at a reference point in the image of the patient anatomy on the display screen that indicates a point of entry into a body cavity of the patient. In further aspects, displaying the representation of the medical instrument may include displaying a three-dimensional representation of the surgical instrument.

In some aspects, the method may further include accessing identifying data associated with the data from the sensors, where the identifying data identifies a particular medical procedure.

In other aspects, the method may further include accessing second data from sensors disposed in a second medical instrument, where the second data includes measured acceleration, rotation, and direction of movement of the second medical instrument. The second data may be correlated with time and associated with the particular medical procedure.

In aspects, the method may further include displaying a representation of a second medical instrument simultaneously with the representation of the medical instrument. In some aspects, the method may further include animating the representation of the second medical instrument based on the second data and correlated time.

In further aspects, the method may further include identifying in the data and in the second data a point when the medical instrument and the second medical instrument are both located at a reference point.

In certain aspects, the method may further include comparing the data and the second data. In certain aspects, comparing the data and the second data may include comparing a difference in elapsed time based on the data and elapsed time based on the second data. In further aspects, comparing the data and the second data may include comparing efficiency based on the data and efficiency based on the second data. In aspects, the method may further include displaying comparison information based on comparison of the data and the second data.

In other aspects, accessing data from a plurality of sensors may include accessing data from an energy actuation sensor. In certain aspects, the method may further include displaying energy usage with the image of the anatomy on the display screen where the energy usage is based on the data from the energy actuation sensor. In some aspects, displaying energy usage may include displaying an expanding marker during a duration of energy actuation.

Still another aspect of the present disclosure is directed to a method of processing sensor measurements. The method includes accessing a plurality of data sets associated with a plurality of medical procedures where each of the plurality of data sets includes data from a plurality of sensors disposed in a medical instrument. The plurality of sensors measure acceleration, rotation, and direction of movement of the medical instrument and each of the plurality of data sets are correlated with time. The method further includes determining, based on the data from the plurality of sensors, at least one of elapsed time of a medical procedure, energy applied in a medical procedure, or efficiency of a medical procedure, and comparing at least one of the elapsed time, the energy applied, or the efficiency among the plurality of medical procedures.

In further aspects, determining elapsed time of a medical procedure may include determining, based on the data from the plurality of sensors, time between the medical instrument being at a reference point and a conclusion of the medical procedure. In aspects, determining efficiency of a medical procedure may include determining, based on the data from the plurality of sensors, energy applied in the medical procedure over the elapsed time of the medical procedure.

In aspects, the method may further include comparing average acceleration among the plurality of data sets. In other aspects, the method may further include identifying one of the plurality of data sets that indicates greatest acceleration among the plurality of data sets.

In certain aspects, the method may further include determining statistical information based on the plurality of data sets.

In some aspects, each of the plurality of data sets may include data from a temperature sensor. The method may further include comparing maximum temperature among the plurality of data sets.

In other aspects, the plurality of data sets may be stored in a cloud storage.

BRIEF DESCRIPTION OF THE DRAWINGS

Various aspects and features of the present disclosure are described hereinbelow with reference to the drawings, wherein.

DETAILED DESCRIPTION

Figure 1:
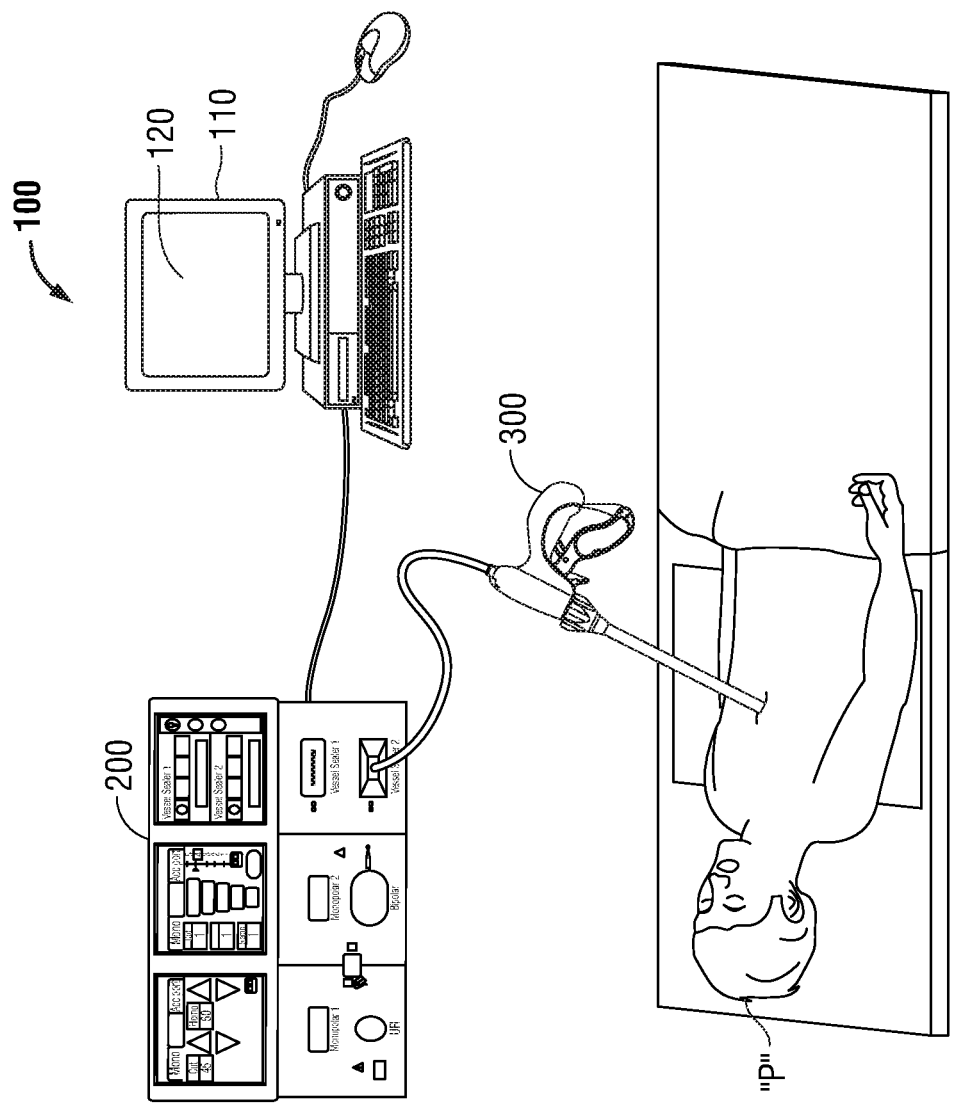
FIG. 1 is a diagram of an exemplary medical system provided in accordance with the present disclosure.

The present disclosure relates to methods and systems for tracking the location of, and data relating to the operation of, a medical instrument during a medical procedure. As detailed herein, a medical instrument in accordance with the present disclosure includes sensors disposed therein that are capable of identifying positional information in multiple degrees of freedom. Specifically, the sensors can include an accelerometer, magnetometer, gyroscope, and/or barometer. These sensors are configured to measure one or more of linear acceleration of the medical instrument, the direction in which the medical instrument is oriented (e.g., yaw and pitch), the orientation of the medical instrument (e.g., roll), and the pressure acting on the medical instrument (e.g., pressure within a patient's body cavity), respectively. The medical instrument may further include a sensor configured to determine an amount of energy applied to tissue during the surgical procedure and/or a sensor configured to measure temperature of tissue during application of electrosurgical energy. The terms "sensor" and "sensors" may be used interchangeably herein such that operations described for one sensor may be performed by or distributed among multiple sensors, and operations described in connection with multiple sensors may be performed by one sensor.

Furthermore, where "sensors" are described as measuring several different quantities, it is contemplated that certain sensors may be responsible for measuring certain quantities, and it is not required for each sensor to measure every quantity.

In aspects of the present disclosure, the disclosed systems and methods determine a point at which the medical instrument enters a body cavity of a patient, correlates the determined point with time, and stores the determined point as a reference point. Data captured by the medical instrument before and/or after the reference point can be used and analyzed relative to the reference point. A representation of a medical instrument may be superimposed on a 3-dimensional (3-D) representation of a patient's body cavity undergoing the medical procedure. The data captured by the sensors in the medical instrument can be utilized to animate the representation of the medical instrument within the 3-D representation of the body cavity. In this manner, the clinician may monitor the precise location, orientation, and heading of the medical instrument within the body cavity. Further, in certain embodiments, the amount of energy applied to tissue by the medical instrument is recorded and represented on the 3-D representation of the body cavity as a circle or sphere. As the energy is applied to tissue over time, the size of the circle or sphere increases correspondingly. In this manner, if energy is applied at multiple locations, the amount of energy applied at each location may be easily perceived (e.g., by illustrating larger or smaller circles or spheres at each location).

The stored data may be stored on any suitable medium, and in some instances may be stored in a cloud storage device. In this manner, data for one or more medical procedures that have been stored as described herein may be compared to one another to compare the length of time of the medical procedures, the amount of energy applied, the pathway of the medical instruments to the area of interest, and other pertinent metrics of the procedures performed by the clinicians. This comparison enables clinicians to receive feedback and to improve medical technique, which ultimately leads to improved patient outcomes.

Although the systems and methods detailed herein are generally described with respect to the abdominal cavity, it is contemplated that the disclosed systems and methods may be applied to other medical techniques or instruments, including minimally invasive surgical techniques or instruments, thoracoscopic surgeries, bronchoscopic surgeries, endoscopic electrosurgical instruments, and laparoscopic electrosurgical instruments, among other medical procedures and instruments.

Embodiments of the present disclosure are now described in detail with reference to the drawings in which like reference numerals designate corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follow, terms such as front, rear, upper, lower, top, bottom, and similar directional terms are used simply for convenience of description and are not intended to limit the disclosure. In the following description, well-known functions or constructions will be understood by persons skilled in the art and may not be described in detail to avoid obscuring the present disclosure in unnecessary detail.

As illustrated in FIG. 1, the methods and systems described herein below utilize a system 100 including a computer 110 and a user interface displayed on a display 120 associated with the computer 110 or on monitoring equipment (not shown). The system 100 further includes an electrosurgical generator 200 and a medical instrument 300 that is in communication with the electrosurgical generator 200. The medical instrument 300 may communicate with the electrosurgical generator 200 through a cable or by using wireless communications. In various embodiments, the medical instrument 300 may communicate certain information to the electrosurgical generator 200 in real time. In various embodiments, the medical instrument 300 may delay communicating certain information to the electrosurgical generator 200 for a period of time. Although generally described herein as being an electrosurgical instrument, the medical instrument 300 may be a medical instrument capable of being used during a minimally invasive surgical procedure or can be other types of medical instruments.

Figure 2:
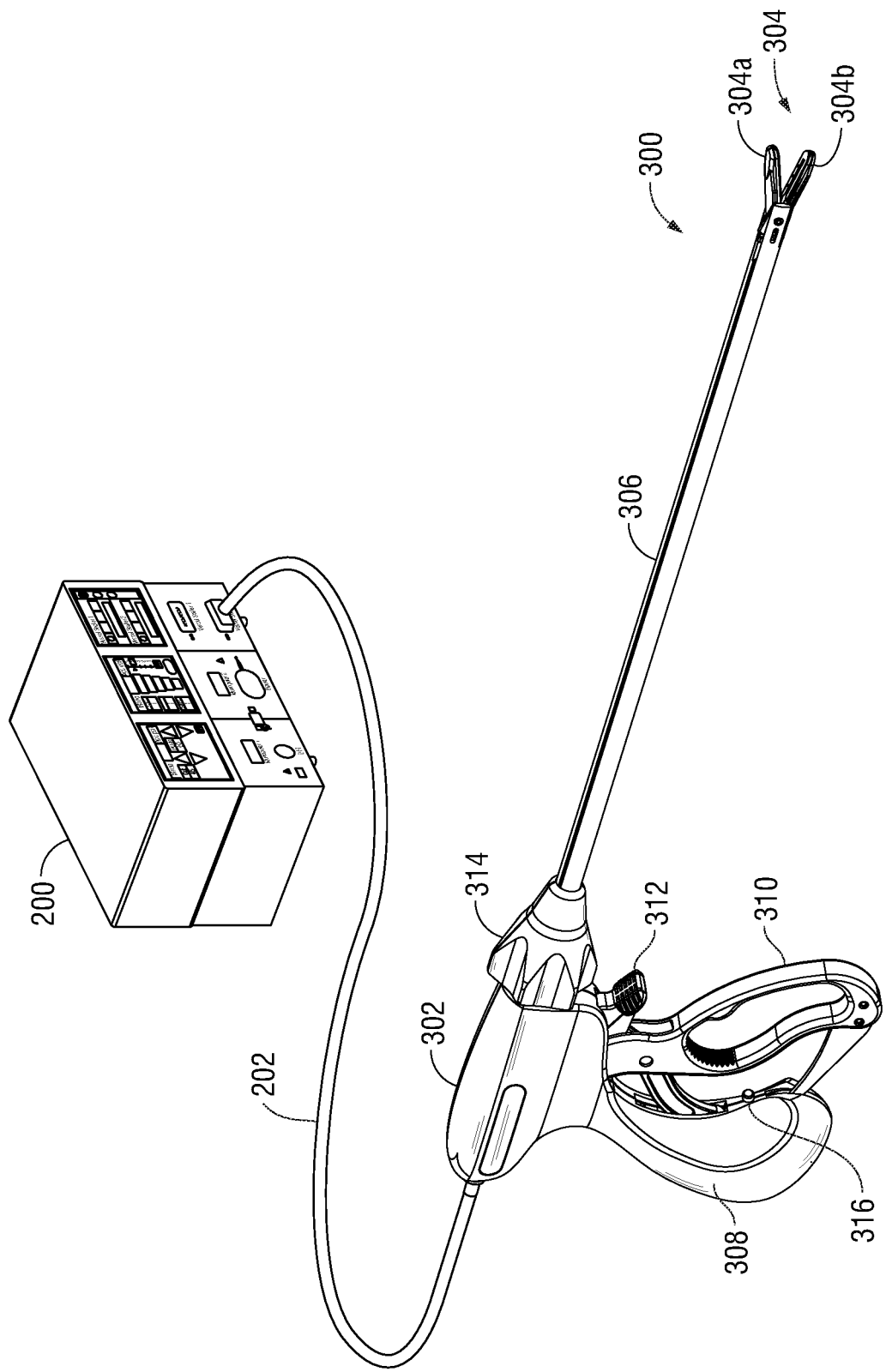
FIG. 2 is a diagram of an exemplary electrosurgical generator and a medical instrument provided in accordance with the present disclosure.
Figure 3:
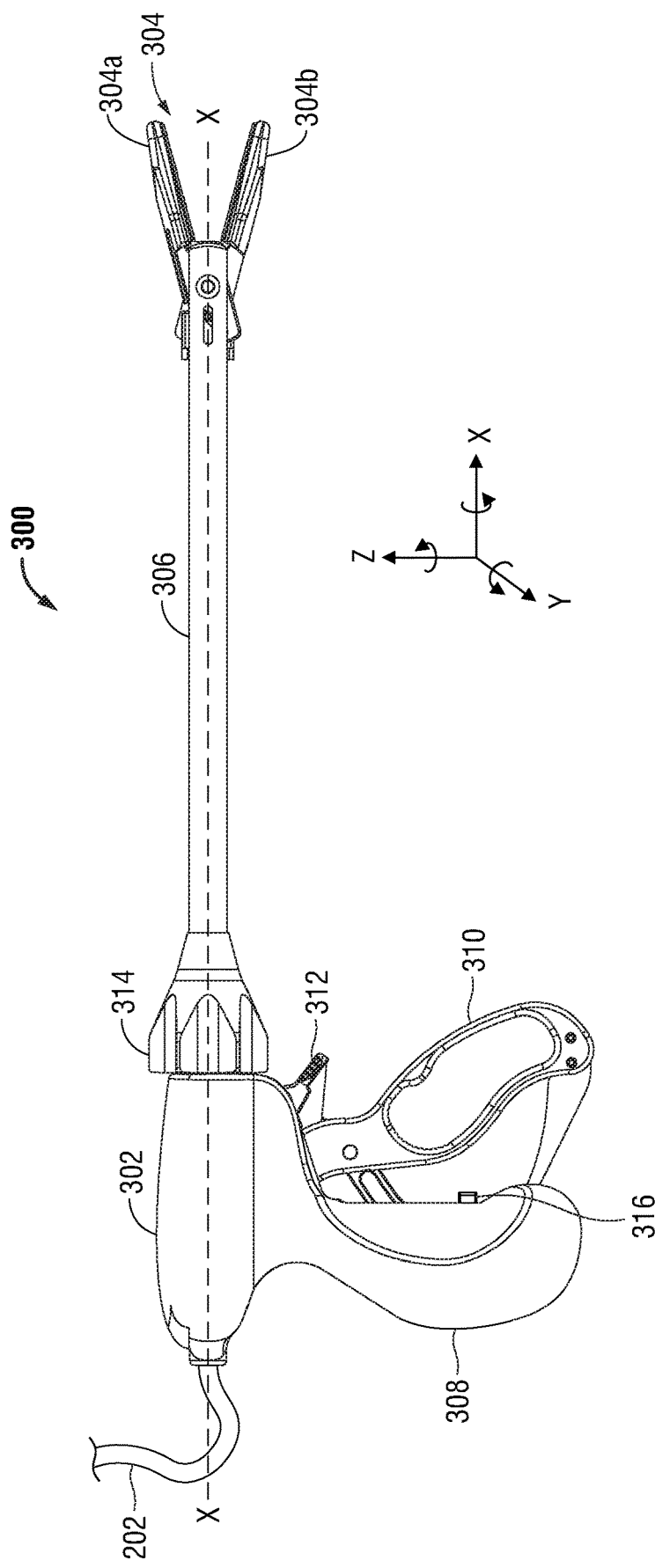
FIG. 3 is a diagram of the medical instrument of FIG. 2.

In the illustrated embodiment in FIG. 2 and FIG. 3, the medical instrument 300 is an electrosurgical forceps having a housing 302 that supports various actuators thereon for remotely controlling an end effector 304 through an elongated shaft 306. The end effector 304 includes a pair of opposed jaw members 304a and 304b that are rotatably supported at a distal portion of the elongate shaft 306. The medical instrument 300 further includes a stationary handle 308 fixedly secured to the housing 302 and a movable handle 310 rotatably supported on the housing 302 such that the movable handle is movable from an open, unactuated position, to a closed, actuated position. The movable handle 310 is in operable communication with the end effector 304 such that actuation of the movable handle 310 from the open, unactuated position to the closed, actuated position, effectuates movement of the opposed jaw members 304a, 304b from a first, open position to a second, approximated position.

A trigger 312 is rotatably supported on the housing 302 of the medical instrument 300 and is operable to extend and retract a knife blade (not shown) slidably disposed within the end effector 304, such that actuation of the trigger 312 effectuates translation of the knife blade to sever tissue grasped between the jaw members 304a, 304b. The housing 302 further includes a rotation knob 314 that is rotatably and translatably supported therein and that is in mechanical communication with the elongated shaft 306. Rotation of the rotation knob 314 effectuates a corresponding rotation of the elongated shaft 306 to place the jaw members 304a, 304b in a desired orientation relative to tissue.

A depressible button 316 is supported on the stationary handle 308 of the medical instrument 300 and is in selective communication with the movable handle 310. In this manner, as the movable handle 310 is actuated from the first, open position, to the second, closed position, the depressible button 316 is depressed by the movable handle 310. The depressible button 316 is operatively coupled with the electrosurgical generator 200, such that actuation of the depressible button 316 initiates delivery of electrosurgical energy to the end effector 314. Further aspects of an exemplary medical instrument capable of being used with the present disclosure are described in U.S. Patent Application Publication No. 2014/0257274, filed Mar. 4, 2014 to McCullough, Jr. et al., entitled "Surgical Instrument," the entire contents of which are hereby incorporated by reference herein.

With continuing reference to FIG. 2, the electrosurgical generator 200 is in electrical communication with the medical instrument 300 by means of a cable 202 extending between the housing 302 of the medical instrument 300 and the electrosurgical generator 200. The electrosurgical generator 200 is capable of providing monopolar or bipolar electrosurgical energy to the medical instrument 300, or another type of energy, such as microwave energy. In embodiments, the electrosurgical generator 200 may include or may be based on electrosurgical generators such as the LigaSure® Vessel Sealing Generator and the ForceTriad® Generator marketed and sold by Covidien.

In accordance with the present disclosure, the system 100 includes sensors capable of measuring information pertaining to the operation of the medical instrument 300. In various embodiments, the sensors cooperate to measure or detect the movement, rotation, orientation, and operation of the medical instrument 300 as it is maneuvered and operated by the clinician. In this manner, the sensors may be capable of detecting motion of the medical instrument 300 in one or more axes, such as, without limitation, a single axis, two axes, three axes, six axes, nine axes, or ten axes. It is contemplated that the sensors may be individually disposed within the housing 302 of the medical instrument 300 at various locations thereof, or may be integrated within an inertial measurement unit (IMU) (not shown) or one or more integrated circuits (not shown) that is disposed within the housing 302 of the medical instrument 300 at a location best suited to measure movement thereof in each of the axes noted hereinabove. It is contemplated that the IMU or integrated circuit may employ microelectromechanical system (MEMS) technology, such as those sold and marketed by Panasonic, Robert Bosch GmbH, InvenSense, Seiko Epson, Sensonor, STMicroelectronics, Freescale Semiconductor, Analog Devices, and various other manufacturers.

Figure 4:
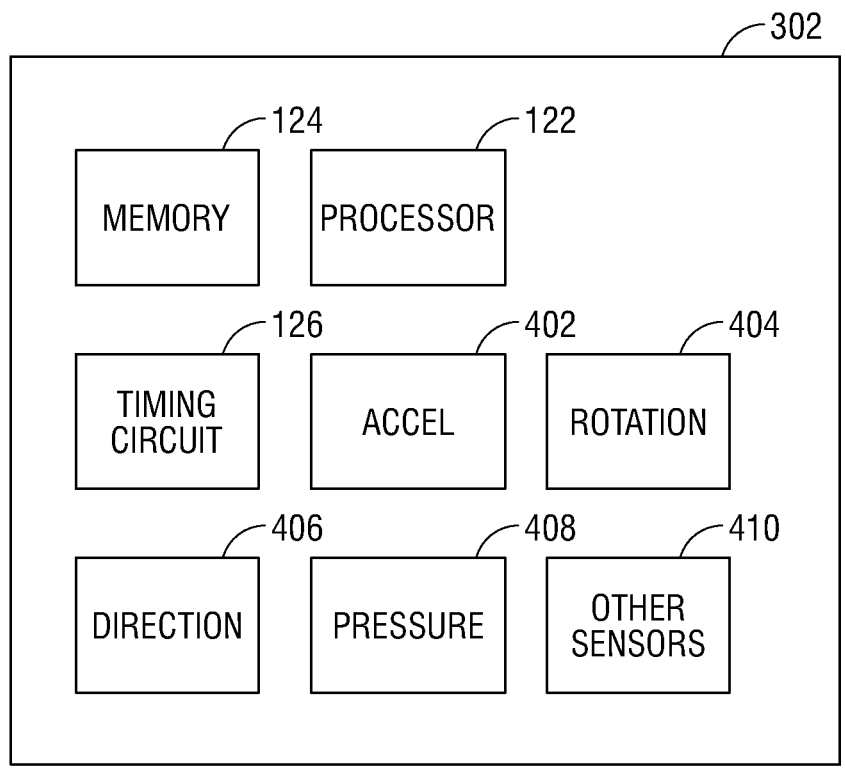
FIG. 4 is a block diagram of the medical instrument of FIG. 1.

Referring now to FIG. 4, there is shown a block diagram of exemplary components of the medical instrument of FIG. 1. The components include sensors 402-410, a processor 122, a memory 124, and a timing circuit 126. The sensors 402-410 communicate measurement data to the processor 122 and the timing circuit 126 communicates a time indication to the processor 122 corresponding to the time when the measurements are obtained. The processor 122 associates the sensor measurement data with the time indication so that they are correlated with each other, and then causes the correlated measurement data and time to be stored in the memory 124. The processor 122 can be a central processing unit, a graphics processing unit, a digital signal processor, a microprocessor, a microcontroller, a programmable logic device, a field-programmable gate array, or an application specific integrated circuit, or another device that can receive sensor measurements and store the measurements in memory. The memory can include random access memory, solid state memory, magnetic storage, and/or another type of storage. In the illustrated embodiment, the sensors 402-410, the processor 122, the memory 124, and the timing circuit 126 are each disposed within the housing 302 of the medical instrument 300. In various embodiments, the sensors 400, the processor 122, the memory 124, and the timing circuit 126 are each disposed on a common printed circuit board (not shown). In various embodiments, some or all of the sensors 402-410 can be implemented and included in one or more integrated circuits. Specifically, it is contemplated that each sensor 402-410 may be disposed within an individual integrated circuit. The configuration of FIG. 4 is exemplary, and other configurations are contemplated, including, for example, the configurations in FIG. 5 and FIG. 6.

Figure 5:
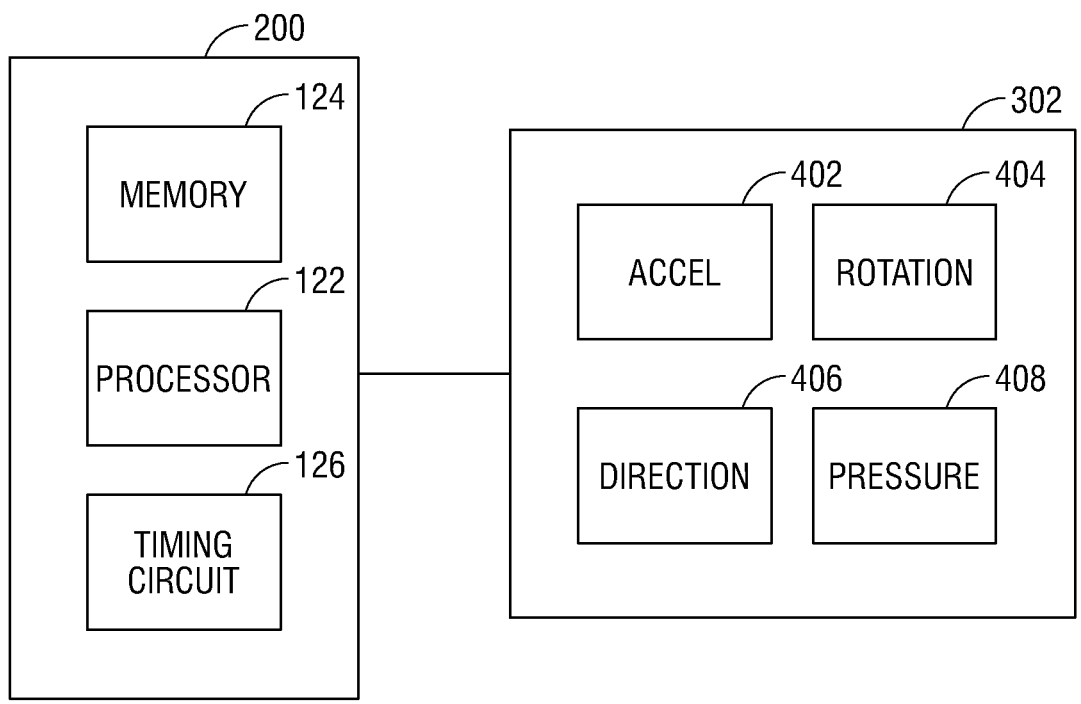
FIG. 5 is a block diagram of the medical instrument and the electrosurgical generator of FIG. 1.
Figure 6:
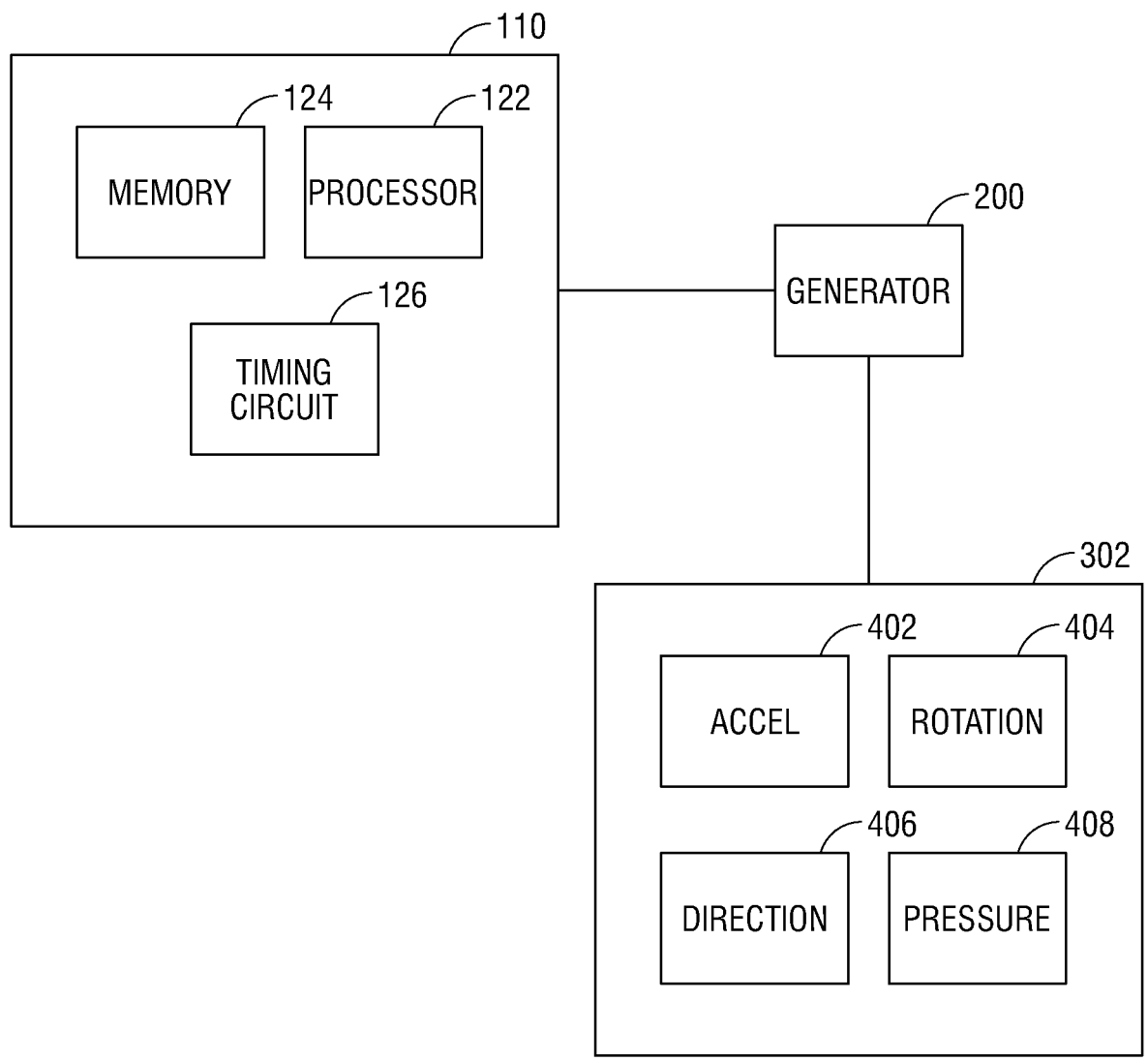
FIG. 6 is a block diagram of a computer operably connected to the electrosurgical generator and the medical instrument of FIG. 1.

In various embodiments, as shown in FIG. 5, it is contemplated that the sensors 402-408 may be disposed within the housing 302 of the medical instrument 300, while the processor 122, the memory 124, and the timing circuit 126 may be disposed within the electrosurgical generator 200 (FIG. 1). In various embodiments, as shown in FIG. 6, the sensors 402-408 may be disposed within the housing 302 of the medical instrument 300, while the processor 122, the memory 124, and the timing circuit 126 may be disposed within the computer 110 (FIG. 1). In this configuration, the medical instrument 300 and the computer 110 can communicate through the electrosurgical generator 200. In other embodiments, the medical instrument 300 and the computer 110 can communicate directly by wireless protocols such as Bluetooth.

Referring again to FIG. 3, and in accordance with various embodiments, the sensors are capable of measuring movement of the medical instrument 300 in nine degrees of freedom (9-DOF); namely, linear acceleration along X, Y, and Z axes, rotation about X, Y, and Z axes, and direction of movement along X, Y, and Z axes. Specifically, a first sensor 402 is capable of measuring linear acceleration of the medical instrument 300 along mutually orthogonal X, Y, and Z axes. The X-axis can extend through proximal and distal portions of the elongated shaft 306 of the medical instrument 300 and align with the elongated shaft 306.

In aspects of the present disclosure, the sensor measurement data can be stored using XML tags that specify the unit of measurement and the measurements along the X, Y, and Z axes. For example:

<acceleration unit=1>
<X>0.10</X>
<Y>0.25</Y>
<Z>−0.60</Z>
<time>011520171330</time>
</acceleration>

In the example above, unit=1 can be meters per second per second, and the sub-tags can include the sensor measurement data in the X, Y, and Z axes and the time associated with the measurements. For example, the time value "011520171300" can represent Jan. 15, 2017, at 13:30. The measurement unit is exemplary and other measurement units are contemplated. Other formats for storing sensor measurement data and the time indicator are also contemplated.

Referring also to FIG. 5, it is contemplated that the first sensor 402 may be any suitable accelerometer capable of measuring linear acceleration, such as a piezoelectric accelerometer, piezoresistive accelerometer, capacitive accelerometer, cantilever beam with proof mass, or the like, although any suitable device capable of measuring linear acceleration may be utilized. In various embodiments, the first sensor 402 is an accelerometer utilizing MEMS technology. The accelerometer may be calibrated during manufacturing of the medical instrument 300 or may be configured using a software application during post-manufacturing processing, as will be described in further detail hereinbelow.

A second sensor 404 is capable of measuring rotational information of the medical instrument 300 in one or more axes as the medical instrument 300 is maneuvered by the clinician, such as measuring yaw, pitch, and/or roll of the medical instrument 300. It is contemplated that the second sensor 404 may be any suitable sensor capable of measuring rotational information, such as a gyroscope, or the like. In various embodiments, the second sensor 404 is a vibrating structure gyroscope manufactured using MEMS technology to measure the rotation of the medical instrument 300 about the longitudinal axis X-X.

A third sensor 406 is capable of measuring directional information of the medical instrument 300 as the medical instrument 300 is maneuvered by the clinician. Specifically, the third sensor 406 is configured to measure movement of the medical instrument 300 as a whole in one or more directions. In this manner, it is contemplated that the third sensor 406 may be a magnetic sensor such as a magnetometer or compass. As can be appreciated, when combined with the data captured by the first sensor 402 and the second sensor 404, the measurement data can be used to enable the clinician to more easily identify the position, orientation, and heading of the medical instrument 300 within a body cavity of a patient. Due to variations in the earth's geomagnetic field, the third sensor 406 is required to be calibrated for each medical instrument 300 depending on the location at which the medical instrument 300 is used. In embodiments, the location of the medical instrument 300 at the time the medical procedure is being performed may be identified either manually, such as by entering a zip code into the computer 110, by entering an address into the computer 110, by entering the location into the computer 110 during initial set-up of the medical instrument 300 or while the medical instrument 300 is undergoing evaluations or being tested, or the like, or automatically, such as by identifying a physical location of the computer 110 based on an IP address or the like, using a sensor (not shown) disposed within the medical instrument 300 that communicates with the Global Positioning System (GPS), by communicating with the hospital's Electronic Medical Records (EMR), or the like. As can be appreciated, the third sensor 406 may be calibrated before each use, or in embodiments, may be calibrated post-operatively using a software application, as will be described in further detail hereinbelow.

In embodiments, it is contemplated that the sensors may include a fourth sensor 408 capable of measuring pressure within the environment in which the medical instrument 300 is located. The fourth sensor 408 may be any suitable barometer or pressure sensor, and in one non-limiting embodiment is a barometer manufactured using MEMS technology. As can be appreciated, when utilized in conjunction with the first, second, and third sensors 402-406, the fourth sensor 408 provides a ten degree of freedom (10-DOF) system to more accurately track the location and orientation of the medical instrument 300 as it is maneuvered by the clinician. It is envisioned that the fourth sensor 408 may be disposed in the IMU or in an integrated circuit, or in embodiments, may be a separate component that is disposed within the housing 302 of the medical instrument 300. As can be appreciated, ambient pressure varies depending on local conditions, such as HVAC equipment, weather patterns, geographical location, etc. Accordingly, it is necessary to calibrate the fourth sensor 408 to the ambient conditions within the operating room. Uses of the pressure measurement data will be described later herein, including using pressure data to determine when a medical instrument or a distal portion of a medical instrument has entered the body cavity of a patient.

Figure 7:
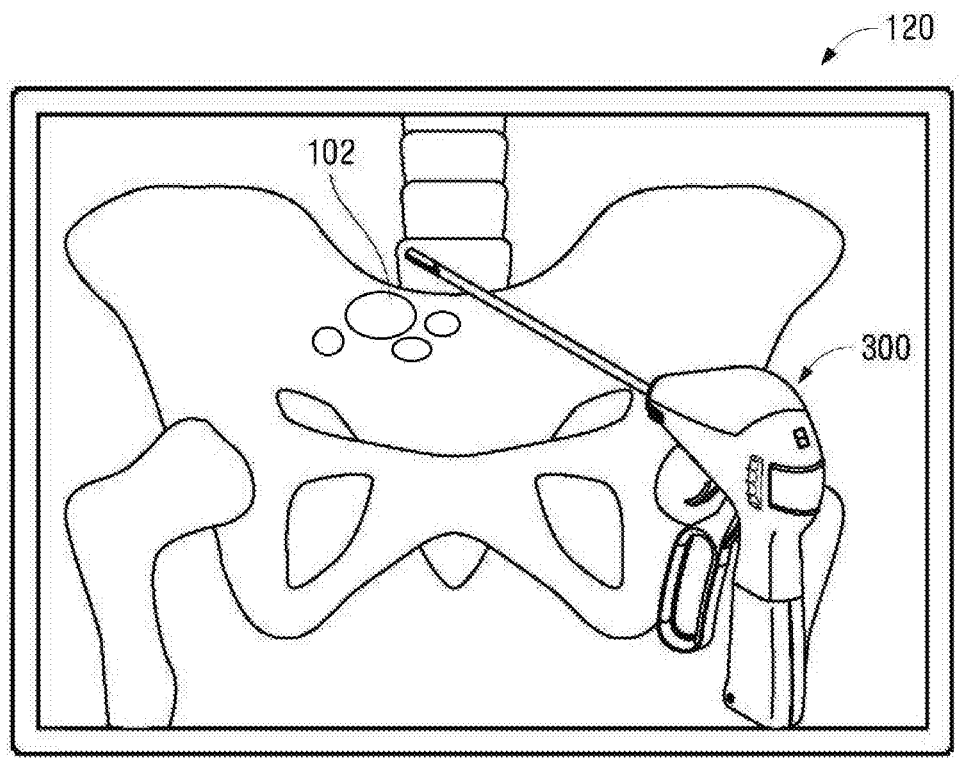
FIG. 7 is an exemplary display image in accordance with the present disclosure.

A fifth sensor (not shown) of the sensors is capable of measuring the amount of energy applied to tissue by the medical instrument 300 or providing data usable to determine the amount of energy applied to tissue. In various embodiments, the fifth sensor can be a power sensor that measure current and voltage of energy applied by the medical instrument 300 to the patient. The current and voltage measurements can be used to determine the amount of energy applied. In various embodiments, the fifth sensor can be a sensor that measures actuation or release of a trigger for applying energy to tissue. The time between trigger actuation and release can be used to determine the amount of energy applied to tissue. The energy applied to tissue is recorded within a memory and is visually represented on the 3-D representation of the body cavity as a circle or sphere 102 (FIG. 7). As the energy applied to the tissue increases, the size of the circle or sphere 102 increases correspondingly. In this manner, if energy is applied at multiple locations, the amount of energy applied at each location may be easily perceived (e.g., by illustrating larger or smaller circles or spheres at each location). Although generally described as being a circle or sphere, it is contemplated that another shape, marking, or indication may be utilized to identify the location at which energy was applied and the amount of energy applied at that location.

In embodiments, the sensors may include a temperature sensor (not shown) capable of measuring the temperature of tissue as electrosurgical energy is applied to tissue. The temperature sensor aids a clinician in determining efficiency of the application of energy and enables the clinician to avoid charring or damaging surrounding tissue.

In various embodiments, some or all of the sensors can be implemented and located in an integrated circuit. In various embodiments, the first, second, third, and fourth sensors described above herein can be located in an integrated circuit. In various embodiments, the sensors can be implemented and located in more than one integrated circuit. Other configurations are contemplated.

Referring again to FIG. 4, the system 100 includes a timing circuit 126 in electrical communication with the processor 122. As described above herein, the timing circuit 126 provides an indication of the time when data is obtained. In this manner, the processor 122 can correlate the time from the timing circuit 126 with measurement data from the sensors and can store the correlated time and data in a memory. For example, with respect to the depressible button 316 of the electrosurgical instrument 300, the processor 122 can correlate a time with depression of the depressible button 316 and correlate another time with release of the depressible button 316, and can compute the elapsed time between button press and button release based on the correlated times.

The data measured by the sensors 402-410 as the medical instrument 300 is maneuvered by the clinician is stored in the memory 124. The memory 124 may include any non-transitory computer-readable storage media for storing data and/or software that is executable by the processor 122, e.g., solid-state, volatile, non-volatile, removable, and non-removable. As can be appreciated, the data collected by the sensors 402-410 and stored in the memory 124 may be transmitted to a local host or to a network location (not shown), such as an electronic medical record database (EMR), cloud storage, or the like, either wirelessly or through a hardwired connection (not shown) such as optical, RS-232, RS485, SPI/I2C, or the like. In various embodiments, the collected data is transmitted using any suitable wireless protocol capable of wirelessly transmitting data either in real time or on demand, such as those conforming to IEEE 802, Zigbee, Bluetooth, or the like. It is further contemplated that the data may be stored on one or more removable storage devices (not shown), such as optical disks (e.g., blu-ray, DVD, CD, or the like), memory cards (e.g., CompactFlash, Secure Digital, Memory Stick, or the like), Zip disks or Floppy Disks, Disk packs, Magnetic tapes, USB flash drives, external hard drives (e.g., IDE, EIDE, SCSSI, DDS, or the like), or the like.

Referring to FIG. 1 and FIG. 4, a software application is stored within the memory 124 and is executed by the processor 122 that is associated with the computer 110 (FIG. 1) to utilize the data stored in the memory 124. For example, the software application can assist a clinician in segmenting a surgical procedure into three or more portions in order to most effectively and efficiently perform the procedure, including at least a pre-operative planning portion, an intra-operative portion, and post-operative review portion.

The pre-operative portion of the surgical procedure typically includes imaging the patient "P" using a suitable imaging system (not shown), such as X-ray CT, computerized axial tomography (CAT) scan, positron emission tomography (PET), and single-photon emission CT (SPECT)). The imaging data may be stored within the memory 124 coupled to the computer 110 (FIG. 1), and/or the imaging data may be stored in any suitable memory. Following imaging of the patient, the software application is executed by the processor 122 to enable review of the image data. An area of interest is identified in the images and its location is determined within the body cavity of the patient "P." Several methods of identifying an area of interest are contemplated, such as ultrasound, CT scan, metabolic scanning, or the like. After analysis, using one of the above described techniques, the location of the area of interest within the body cavity may be identified and its location stored within the memory 124 coupled to the computer 110 (FIG. 1).

The image data is processed by the software application to generate a 3-D reconstruction of the patient body cavity. In one non-limiting embodiment, the 3-D reconstruction is generated using the techniques described in U.S. Patent Application Publication No. 2016/0038248 to Bharadwaj et al. entitled "Treatment Procedure Planning System and Method," filed Aug. 10, 2015, the entire contents of which are incorporated by reference herein. The 3-D reconstruction is displayed on the display 120 (FIG. 1) or suitable monitoring equipment (not shown), as shown in FIG. 7. In embodiments, the software application may display a two-dimensional representation of the patient's body cavity, and persons skilled in the art will understand the techniques for doing so.

The clinician may utilize the software application to determine a pathway through which surgical tools, such as the medical instrument 300, may be advanced within the patient "P." Additionally, the software application may identify an optimal location at which a trocar or access port (not shown) may be introduced to most easily reach the area of interest using the medical instrument 300. This location of an access point can be stored as a "reference point," which will be described in more detail later herein. This access point and pathway may be illustrated on the display 120 associated with the computer 110 (FIG. 1) or on the monitoring equipment. Using the measurement data captured by the sensors 402-410, the position and progress of the medical instrument 300 may be displayed as the medical instrument 300 is advanced within the body cavity of the patient "P," as shown in FIG. 7. It is further contemplated that the pathway may be superimposed on video images captured by a laparoscope or any other suitable device capable of being advanced within a patient "P" to capture images. It is envisioned that any suitable software application capable of generating a pathway to the area of interest may be utilized.

Figure 8:
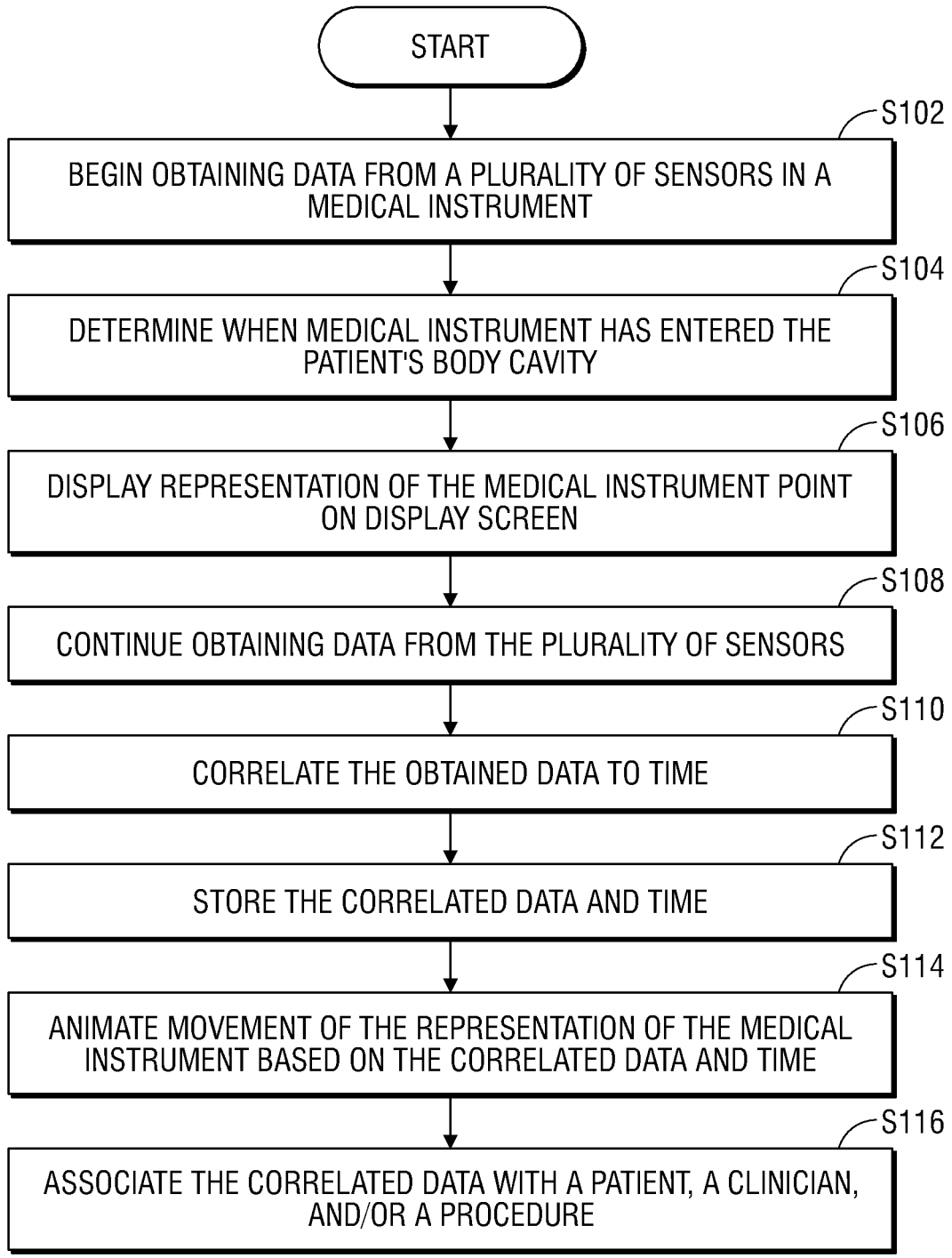
FIG. 8 is a flow chart of an exemplary intraoperative method in accordance with the present disclosure.

Once pre-operative planning is complete and the 3-D representation of the body cavity has been generated, the surgical procedure may begin. Referring to FIG. 8, there is shown a flow diagram of a method of obtaining and using sensor measurement data in accordance with the present disclosure. Before advancing the medical instrument 300 within the body cavity, in step S102, the clinician initiates the capture and recording of the data from the sensors, which can be activated, for example, using a user interface on the computer 110 (FIG. 1) or by depressing a button (not shown) disposed on the housing 302 of the medical instrument 300. The medical instrument 300 is advanced to a trocar (not shown) or another surgical access device. In step S104, the processor determines when a distal portion of the medical instrument 300 has entered the body cavity of the patient "P." This determination may be made using several methods. In one embodiment, the software application uses data captured by the first sensor 402 (e.g., accelerometer) to identify when the medical instrument 300 has entered the body cavity of the patient. For example, as the medical instrument 300 is advanced within the trocar, acceleration of the medical instrument 300 is greatly reduced compared to acceleration of the medical instrument 300 outside the patient's body cavity. Once the medical instrument 300 has entered the body cavity of the patient, the progress of the medical instrument 300 is considerably smoother and slower, resulting in reduced variation in linear acceleration measurements. The software application identifies the transition point between measurements, such as the time when the measured acceleration decreases from above a first threshold stored in the memory 124 to below a second threshold stored in the memory 124, and determines that time to be when the medical instrument 300 has entered the body cavity of the patient through the access point. As can be appreciated, the first sensor 402 and the third sensor 406 may be required to be calibrated using the software application before beginning the surgical procedure and recording the data.

In various embodiments, it is contemplated that the fourth sensor 408 (e.g., barometer) may identify a change in ambient pressure as the medical instrument 300 enters the body cavity of the patient. Specifically, the pressure within the body cavity of the patient is greater than the ambient pressure of the operating room. Initially, the fourth sensor 408 is calibrated for the location in which the surgical procedure is being performed to ensure accurate pressure measurements are captured by the fourth sensor 408. When the medical instrument 300 is advanced within the trocar, the software application identifies the change in pressure. In various embodiments, the software application determines that the medical instrument 300 has entered the body cavity of the patient when the pressure measured by the fourth sensor 408 exceeds a certain pressure threshold that is stored in the memory 124. Other ways of determining when the medical instrument 300 has entered the body cavity of a patient are contemplated. For example, in embodiments, the clinician may depress a trigger or button (not shown) disposed on the housing 302 of the medical instrument 300 to indicate that the medical instrument 300 has entered the body cavity of the patient.

The time at which the software application determines that the medical instrument 300 has entered the body cavity of the patient can be designated as a reference time point and stored in the memory 124. As discussed above herein, the reference location/access point for accessing the body cavity of a patient is displayed on the 3-D representation of the patient's anatomy.

Once the software application determines that the medical instrument 300 has entered the body cavity of the patient, in step S106, a representation of the medical instrument 300 is displayed and superimposed over the 3-D representation of the body cavity. The sensors continually obtain data relating to the position, orientation, and operation of the medical instrument during the surgical procedure in step S108. In embodiments, the position and orientation of the displayed representation of the medical instrument 300 may be continually updated according to the data obtained by the sensors in real time. In this manner, the clinician may observe the progress of the medical instrument 300 as it is advanced within the body cavity of the patient and, in embodiments, follow the pathway generated during pre-operative planning. It is further contemplated that the clinician may mark, on the display screen, specific landmarks or points of interest within the body cavity, which may be stored in the memory 124 for review by the clinician at a later date.

In step S110, the data that is obtained by the sensors is correlated with time, as described hereinabove. The correlated data and time are stored in the memory 124 in step S112. In various embodiments, steps S108-S112 can operate until the medical instrument 300 or the sensors are turned off. In step S114, the correlated data and time can be used to animate the displayed representation of the medical instrument 300. In various embodiments, step S114 can operate during a medical procedure and can operate until the medical instrument 300 or the sensors are turned off. In various embodiments, step S114 can operate after a medical procedure is completed, as a "playback" of the procedure, which allows clinicians to study and/or identify potential areas of improvement, as will be described in further detail hereinabove.

In step S116, the correlated data and time can be associated with the particular patient, the particular clinician performing the surgical procedure, the procedure being performed, or various other characteristics. For example, without limitation, identifying information relating to the patient can include the patient's condition, age, sex, height, weight, race or national origin, or the like, the disease type and planned procedure, and the patient's medical history. Further, the images obtained during pre-operative planning can also be associated with each patient. As can be appreciated, over time, a database may be built using the data obtained during each procedure. This database may be indexed such that clinicians may review data obtained from similar patients or procedures for comparison, as will be described in further detail hereinbelow.

Figure 9:
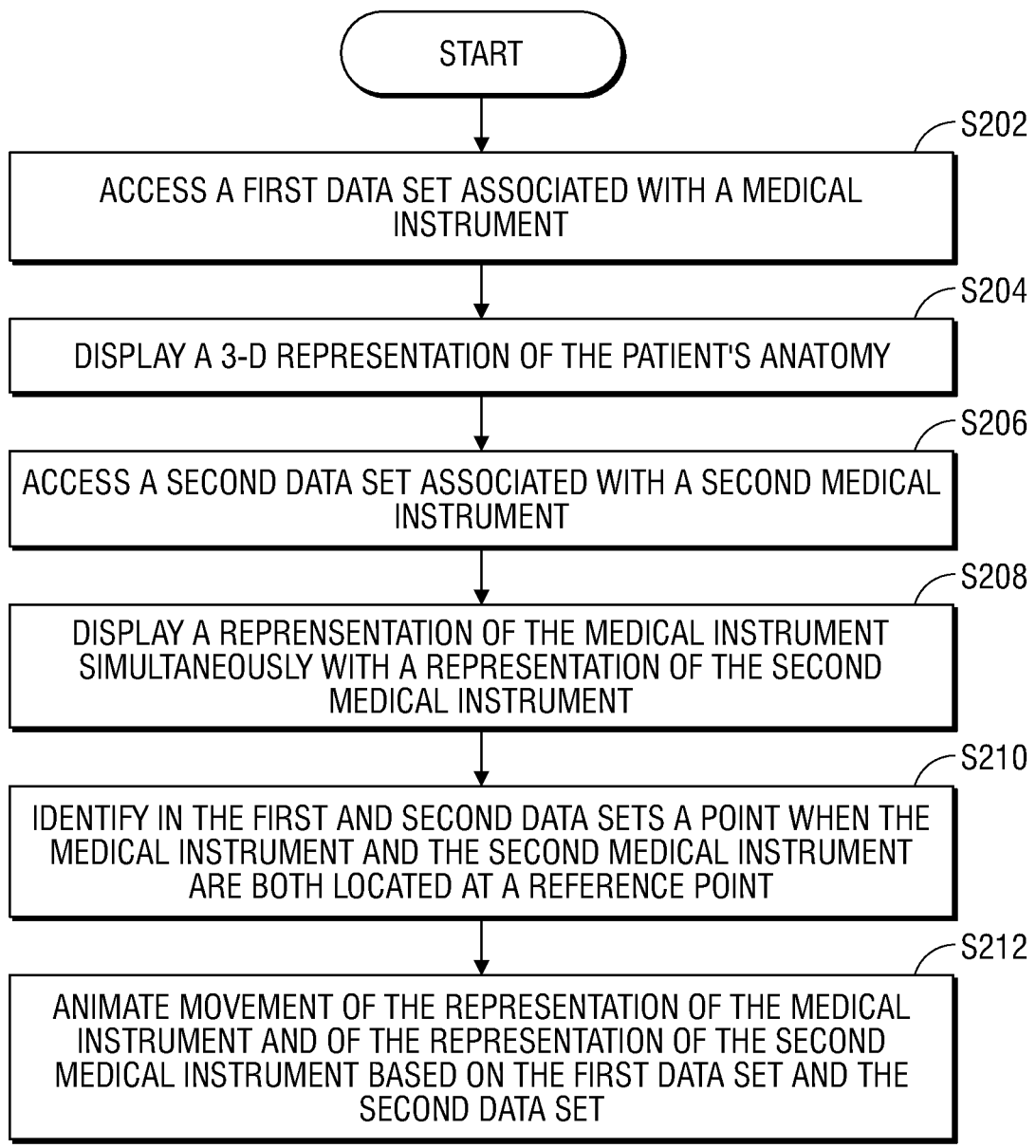
FIG. 9 is a flow chart of an exemplary post-operative method in accordance with the present disclosure.

Turning to FIG. 9, there is shown a flow diagram of a method of using sensor measurement and time data. In step S202, a first data set that has been associated with a medical instrument 300 is accessed from the memory 124. The first data set includes sensor measurement data obtained from the medical instrument 300 and time indications correlated therewith. As can be appreciated, the stored data may be accessed using any device capable of running the software application. It is envisioned that the stored data may be accessed remotely or locally via a computer or other similar device that is connected to the local area network that is coupled to the memory 124. In step S204, a 3-D representation of the patient's body cavity is displayed on the device used to access the first data set. The 3-D representation can be the model generated during pre-operative planning associated with the first data set obtained in step S202. A second data set associated with a second medical instrument is accessed in step S206. The second data set includes sensor measurement data obtained from the second medical instrument and time indications correlated therewith. The second medical instrument may have been used on either the same patient or a different patient. As can be appreciated, this second data set may be selected by the clinician or may be automatically identified by the software application. For example, it is contemplated that the software application may compare the first data set to other data sets in a database, and using various characteristics, identify another data set or other data sets which have the same or similar characteristics as the first data. It is envisioned that the software application may assign a similarity percentage or other metric (e.g., ranking, number of similar characteristics, or the like) to data sets stored within the database, such that the other data set may be considered a 100% match, 95% match, or the like, when compared to the first data set. It is further contemplated that the software application may rank or otherwise compile, in descending or ascending order, a list of identified data sets. Using this information, the clinician may make a selection of the second data set for comparison, as will be described in further detail hereinbelow.

In step S208, a representation of the medical instrument associated with the first data set is displayed and superimposed on the 3-D representation of the patient body cavity simultaneously with a representation of a second medical instrument associated with the second data set. The representations of the medical instrument and the second medical instrument can be three-dimensional representations. In step S210, the point at which each of the first and second medical instruments entered the body cavity of the patient is identified in the first and second data sets, although it is contemplated that any suitable reference point may be used in order to correlate the first data set to the second data set. As can be appreciated, the first data set and the second data set must be registered such that each procedure may be played back with respect to a common reference point. The representations of the first and second medical instrument are animated in step S212 based on the first data set and the second data set respectively. In this manner, the clinician may identify differences between each medical procedure in order to assess ways to improve surgical techniques, such as improving navigation of the medical instrument to the area of interest, the amount of electrosurgical energy used during the medical procedure, the amount of time required to complete the medical procedure, the accuracy in treating the area of interest, and/or collateral trauma, among other things. As can be appreciated, the clinician may select additional data sets, such as a third data set, a fourth data set, etc., and display representations of medical instruments corresponding thereto on the display screen.

What have been described above are systems and methods for obtaining measurement data from sensors in medical instruments and using the data to display uses of the instruments in medical procedures. The following describes uses of the sensor measurement data for comparing efficiency and/or other aspects of medical procedures tracked and recorded in accordance with the present disclosure.

Figure 10:
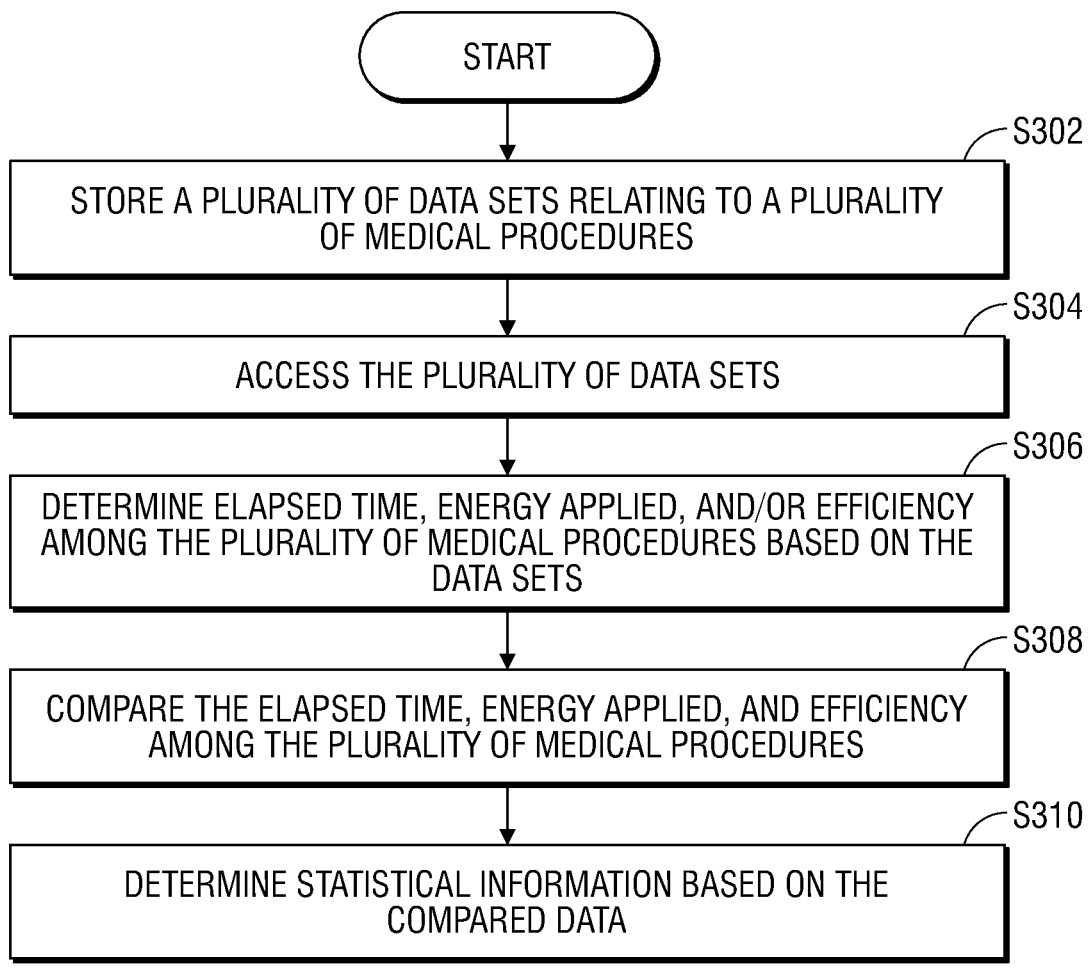
FIG. 10 is a flow chart of another post-operative method in accordance with the disclosed technology.

It is contemplated that the database storing the data sets may be accessible using a private network or shared via a public network accessible by individuals remotely located from the storage device used to store the data sets. With reference to FIG. 10, data sets in accordance with the present disclosure are stored in the database in step S302. In step S304, a user accesses the database and the data sets via the software application and may select one or more data sets using a device (e.g., the computer 110, a personal computer, a tablet, a smartphone, or the like) capable of executing the software application. In step S306, the software application calculates or determines metrics for the medical procedures corresponding to the selected data sets, such as elapsed time of the medical procedure, amount of energy applied during the medical procedure, efficiency of the medical procedure, and collateral trauma, among other metrics.

In various embodiments, elapsed time can be calculated based on the time a medical instrument enters a body cavity of a patient to the time when the medical device or sensors are turned off. The amount of energy used can be computed in various ways depending on the type of sensor measurements recorded. For example, if sensor measurements for voltage and current of energy applied by a medical instrument are recorded, the current and voltage measurements can be used to determine the amount of energy applied during the medical procedure. As another example, if sensor measurements for trigger actuation and release are recorded, the amount of energy applied can be computed based on the time of trigger actuation and the time of trigger release, and based on information about the particular medical instrument that was used. In various embodiments, efficiency of a medical procedure can be determined in different ways. For example, efficiency can be determined based simply on the duration of the medical procedure, or based on the total amount of energy applied, or based on the amount of energy applied per unit time (e.g., per minute or per hour) during the medical procedure.

The calculated metrics for each data set is compared in step S308, and in step S310, the software application determines statistical information relating to the compared data. For example, the statistical information can include minimum, maximum, mean, median, mode, range, variance, standard deviation, and/or correlation metrics, for the data in the data sets. For example, average acceleration and maximum acceleration among the data sets can be computed and compared, and the data set indicating the greatest acceleration can be identified. In various embodiments, maximum tissue temperature can be compared, and the data set indicating the highest temperature can be identified. In this manner, the differences between the metrics associated with each medical procedure may be displayed to the user such that the user may ascertain various ways to improve his or her technique when performing the surgical procedure in the future.

It is further contemplated that the software application may display suggestions or identify areas for improvement based on the other selected medical procedures. In particular, it is envisioned that the software application may divide the data sets into subsets, such as in a tree format (e.g., parent/child relationship) or in any other suitable representation that enables a user to focus on data of interest. Additionally, it is contemplated that the software application may enable a user to take snap-shots or capture portions of the data for dissemination or sharing with other surgeons or clinicians for a more focused review of the selected surgical procedure. In this manner, a peer review process may be employed to further enhance the ability of clinicians to improve surgical techniques. Specifically, clinicians may anonymously compare surgical procedures in an effort to identify differences between an individual's performance and the standard of quality for the field of the medical procedure. In this manner, the surgical procedure may be associated with an anonymous clinician, rather than revealing the clinician's name or any other identifying information. In embodiments, the data sets may be linked to surgical outcomes to identify trends in surgical actions for the most successful procedures. As can be appreciated, clinicians may select the most successful procedures to compare against their own in an effort to further improve their surgical techniques. It is further contemplated that the software application may enable clinicians to telestrate or use other similar techniques to enable clinicians or educators to effectively illustrate important aspects of the procedure. In embodiments, clinicians may keep a log of surgical procedures that they have performed in order to identify trends in energy use, efficiency of movement (e.g., maximum acceleration, total distance traveled, degree of tilt, rotation, camber, etc.), efficiency of time (e.g., time spent at a particular location or section of the patient's body), and procedural consistency, among other characteristics or metrics.

Additionally, the software application may determine the average acceleration measured by the first sensor 402 amongst the selected data sets. In a similar fashion, it is contemplated that the maximum acceleration measured by the first sensor 402 amongst the selected data sets may be identified along with the maximum temperature measured by the temperature sensor amongst the selected data sets. By indicating these metrics, clinicians may select the procedures having these characteristics and study the data to determine why the acceleration, temperature, or the like was applied in that particular manner.

While several embodiments of the disclosure have been shown in the drawings, it is not intended that the disclosure be limited thereto, as it is intended that the disclosure be as broad in scope as the art will allow and that the specification be read likewise. The disclosed embodiments may be combined in various combinations not expressly disclosed or described herein, and such combinations of embodiments are contemplated to be within the scope of the present disclosure. Therefore, the above description should not be construed as limiting, but merely as exemplifications of particular embodiments.

What is claimed is:

1. A method for a medical procedure, comprising:
   obtaining a plurality of data sets from a respective plurality of sensors disposed in a medical instrument, the plurality of sensors comprising at least one first sensor configured to measure acceleration, at least one second sensor configured to measure rotation, and at least one third sensor configured to measure direction of movement;
   determining, based on a decrease in measured acceleration from above a first threshold to below a second threshold, a time at which the medical instrument transitions from being positioned outside a patient's body to being positioned within the patient's body cavity via the medical device entering the patient's body cavity through an access point;
   displaying a representation of the access point through which the medical instrument enters the patient's body cavity;
   correlating each of the obtained plurality of data sets from the respective plurality of sensors with a time when the plurality of data sets was obtained;
   determining, for each of the obtained plurality of data sets, a maximum acceleration of the medical instrument;
   comparing the determined maximum acceleration from each of the obtained plurality of data sets;
   identifying which of the plurality of obtained data sets indicates a greatest maximum acceleration;
   storing the correlated plurality of data sets and the correlated times;
   accessing the stored correlated plurality of data sets and the stored correlated times after a medical procedure has been completed; and displaying and animating movement of a representation of the medical instrument based on the accessed correlated plurality of data sets and time the accessed correlated times, wherein the representation of the medical instrument is superimposed over a three dimensional (3D) representation of the patient's body cavity and animating movement of the superimposed representation of the medical instrument is in real time.

2. The method of claim 1, wherein the at least one first sensor includes an accelerometer, the at least one second sensor includes a gyroscope, and the at least one third sensor includes a magnetometer.

3. The method of claim 2, wherein the plurality of sensors includes at least one fourth sensor configured to measure pressure, the at least one fourth sensor including a barometer.

4. The method of claim 3, further comprising determining that the medical instrument has entered the body cavity of the patient by determining that measured pressure from the barometer exceeds a threshold.

5. The method of claim 4, wherein obtaining the plurality of data sets from the respective plurality of sensors includes obtaining the plurality of data sets from the respective plurality of sensors as the medical instrument is maneuvered within the body cavity of the patient.

6. The method of claim 1, further comprising associating the correlated plurality of data sets with at least one of the patient, a particular clinician, or a particular medical procedure.

7. The method of claim 1, further comprising:
animating movement of the superimposed representation of the medical instrument in real time as the medical instrument is moved within the patient's body cavity.

8. A medical system comprising:
at least one first sensor disposed in a medical instrument and configured to measure acceleration;
at least one second sensor disposed in the medical instrument and configured to measure rotation;
at least one third sensor disposed in the medical instrument and configured to measure direction of movement;
a clock circuit configured to indicate time;
a memory; and
processing circuitry in communication with the at least one first sensor, the at least one second sensor, the at least one third sensor, and the clock circuit, the processing circuitry configured to:
receive a measured data set from each of the at least one first sensor, the at least one second sensor, and the at least one third sensor;
determine, based on a decrease in measured acceleration from above a first threshold to below a second threshold, a time at which the medical instrument transitions from being positioned outside a patient's body to being positioned within the patient's body cavity via the medical device entering the patient's body cavity through an access point;
display a representation of the access point through which the medical instrument enters the patient's body cavity;
correlate each of the measured data sets with a time indicated by the clock circuit at which the measured data sets were measured;
determine, for each of the measured data sets, a maximum acceleration of the medical instrument;
compare the determined maximum acceleration from each of the measured data sets;
identify which of the measured data sets indicates a greatest maximum acceleration;
store the correlated measured data sets and the correlated times in the memory;
access the stored correlated data sets and the stored correlated times after a medical procedure has been completed; and
display and animate movement of a representation of the medical instrument based on the accessed correlated data and the accessed correlated times, wherein the representation of the medical instrument is superimposed over a three dimensional (3D) representation of the patient's body cavity and animating movement of the superimposed representation of the medical instrument is in real time.

9. The medical system of claim 8, wherein the at least one first sensor includes an accelerometer, the at least one second sensor includes a gyroscope, and the at least one third sensor includes a magnetometer.

10. The medical system of claim 9, wherein:
the accelerometer is configured to measure linear acceleration of the medical instrument;
the gyroscope is configured to measure at least rotation of the medical instrument about a longitudinal axis of the medial instrument; and
the magnetometer is configured to measure direction of the medical instrument based on a geomagnetic field.

11. The medical system of claim 8, wherein the at least one second sensor is configured to measure at last one of yaw, pitch, or roll of the medical instrument.

12. The medical system of claim 8, further including at least one fourth sensor disposed in the medical instrument configured to measure pressure, energy applied to the patient by the medical instrument, or combinations thereof.

13. The medical system of claim 12, further comprising an integrated circuit disposed in the medical instrument, the integrated circuit including the at least one first sensor, the at least one second sensor, the at least one third sensor, and the at least one fourth sensor.

14. The medical system of claim 12, wherein the processing circuitry is configured to determine that a distal portion of the medical instrument has entered the body cavity of the patient based on measured pressure from the at least one fourth sensor exceeding a threshold.

15. The medical system of claim 8, wherein the memory is configured to store at least one of a medical instrument identifier, a clinician identifier, or a medical procedure identifier, the at least one stored identifier being associated with the correlated measured data sets.

16. The medical system of claim 8, further comprising a trigger disposed on the medical instrument and in communication with the processing circuitry, the processing circuitry configured to determine an amount of time the trigger is actuated to determine an amount of energy applied to the patient by the medical instrument.

17. The medical system of claim 8, further comprising a trigger disposed on the medical instrument and in communication with the processing circuitry, the processing circuitry configured to register an actuation of the trigger and a release of the trigger to determine an amount of energy applied to the patient by the medical instrument.

18. The medical system of claim 8, further comprising a trigger disposed on the medical instrument and in communication with the processing circuitry, wherein the processing circuitry is configured to determine that a distal portion of the medical instrument has entered the body cavity of the patient when the trigger is actuated.

19. The medical system of claim 8, wherein the processing circuitry is configured to:

animate movement of the superimposed representation of the medical instrument in real time as the medical instrument is moved within the patient's body cavity.

20. A method for tracking use of a medical instrument, comprising:

obtaining a plurality of data sets from a respective plurality of sensors disposed in a medical instrument, the plurality of sensors comprising at least one first sensor configured to measure acceleration, at least one second sensor configured to measure rotation, and at least one third sensor configured to measure direction of movement;

determining, based on a decrease in measured acceleration from above a first threshold to below a second threshold, the time at which the medical instrument transitions from being positioned outside a patient's body to being positioned within the patient's body cavity via the medical device entering the patient's body cavity through an access point;

displaying a representation of the access point through which the medical instrument enters the patient's body cavity;

displaying a representation of the medical instrument superimposed over a three dimensional (3D) representation of the patient's body cavity;

animating movement of the superimposed representation of the medical instrument in real time as the medical instrument is moved within the patient's body cavity;

correlating each of the obtained plurality of data sets from the respective plurality of sensors with a time when the plurality of data sets was obtained;

determining, for each of the obtained plurality of data sets, a maximum acceleration of the medical instrument;

comparing the determined maximum acceleration from each of the obtained plurality of data sets;

identifying which of the plurality of obtained data sets indicates a greatest maximum acceleration; and storing the correlated plurality of data sets and the correlated times.

\* \* \* \* \*